United States Patent [19]
Grimberg et al.

[11] Patent Number: 5,609,821
[45] Date of Patent: Mar. 11, 1997

[54] PROCESS FOR THE TREATMENT OF AN ARTICLE AND A NEW AQUEOUS HYDROGEN PEROXIDE SOLUTION

[75] Inventors: Aurélie Grimberg, Rostock, Germany; Gérard DeClerck, Saint-Gratien, France; Jean-Marc Rabillier, Guyancourt, France; Raymond Soumarmon, Noisy Le Sec, France

[73] Assignee: Chemoxal S.A., Paris, France

[21] Appl. No.: 279,209

[22] Filed: Jul. 22, 1994

[30] Foreign Application Priority Data

Jul. 22, 1993 [FR] France .................... 93 09061

[51] Int. Cl.$^6$ .................... A61L 2/18; C01B 15/037
[52] U.S. Cl. .................... 422/28; 422/27; 422/292; 252/186.28; 252/186.29
[58] Field of Search .................... 422/28, 27, 292; 252/186.28, 186.29

[56] References Cited

U.S. PATENT DOCUMENTS

| | | | |
|---|---|---|---|
| 3,234,140 | 2/1966 | Irani | 252/186.29 |
| 4,034,064 | 7/1977 | Cook, Jr. | 423/272 |
| 4,059,678 | 11/1977 | Winkley | 252/186.28 |
| 4,401,509 | 8/1983 | Schellinger, Jr. | 156/666 |
| 5,007,232 | 4/1991 | Caudill | 422/28 |
| 5,130,053 | 7/1992 | Feasey et al. | 252/400.22 |
| 5,258,162 | 11/1993 | Andersson et al. | 422/28 |
| 5,368,828 | 11/1994 | Carlson | 422/300 |
| 5,484,453 | 1/1996 | Baehr et al. | 8/111 |

FOREIGN PATENT DOCUMENTS

| | | |
|---|---|---|
| 0265381 | 4/1988 | European Pat. Off. . |
| 1271518 | 8/1961 | France . |
| 1449711 | 8/1966 | France . |
| 1473779 | 3/1967 | France . |
| 79/01074 | 12/1979 | WIPO . |

*Primary Examiner*—Richard D. Lovering
*Assistant Examiner*—Joseph D. Anthony
*Attorney, Agent, or Firm*—Burns, Doane, Swecker & Mathis, L.L.P.

[57] ABSTRACT

A process for disinfecting or sterilizing an article comprising spraying on at least one surface of the article an aqueous hydrogen peroxide solution including an organic phosphonic acid in an amount effective to stabilize said hydrogen peroxide solution, said solution being free of other stabilizing agents.

21 Claims, No Drawings

PROCESS FOR THE TREATMENT OF AN ARTICLE AND A NEW AQUEOUS HYDROGEN PEROXIDE SOLUTION

BACKGROUND OF THE INVENTION

(i) Field of the Invention

The present invention relates to a process for the treatment of an article by spraying on at least one of its surfaces an aqueous hydrogen peroxide solution, notably with a view to disinfect or sterilize the article, as well as to a novel aqueous hydrogen peroxide solution which can be employed in such process.

(ii) Description of Related Art

It is known that the disinfection or sterilization of articles such as food products or packaging materials such as packagings for cosmetics, pharmaceuticals or foodstuffs can be carried out by means of aqueous hydrogen peroxide solutions. In this regard, the article to be treated can, for example, be soaked in a bath comprised of an aqueous hydrogen peroxide solution or the article can be sprayed by means of such an aqueous solution.

Generally, for best efficiency, the aqueous hydrogen peroxide solution which is utilized is hot, Spraying processes permit optimum contact of the aqueous hydrogen peroxide solution with all the surfaces of the treated article.

After spraying, the article is typically dried, for example with sterile hot air, in order to eliminate all traces of hydrogen peroxide from the treated surface. The spraying is carried out with a spraying system, for example with spray jets. When the aqueous hydrogen peroxide solution which is sprayed on the article is hot, the spraying system can include, at the outlets of the spray jets, a device of the THERMOCOAX® type, containing a tube and a coaxial heating element, which permits the aqueous hydrogen peroxide solution to be brought to the desired temperature. This tube can also contain in known manner the means permitting the best dispersion of the aqueous hydrogen peroxide solution on the surface of the treated article. Such a means can notably comprise springs and gimlets.

However, the hydrogen peroxide solutions typically employed in this type of process lead to the formation of a deposit and to progressive fouling of the spraying system as well as to jamming of moveable mechanical parts.

It is therefore necessary to regularly clean, generally on a daily basis or, at best, once every two days, the spraying system, failing which such system becomes completely blocked. Such frequent cleaning of the spraying system requires stopping of the treatment process which naturally leads to a reduction in the yield as well as to an increase in the cost of production, The applicant has been able to demonstrate that the fouling of the spraying system can to a large extent be attributed to the nature of the stabilization agent contained in the aqueous hydrogen peroxide solution.

Classical stabilization agents include phosphoric acid, tin oxides, such as sodium stannate, dipicolinic acid, sodium pyrophosphate acid, or organic phosphonic acids or their salts. The organic phosphonic acids are typically only utilized in combination with other stabilizing agents and particularly the tin oxides. Such combinations are for example described in patent FR-1,473,779. The use of organic phosphonic acids which are not associated with other stabilizing agents has only been described for very particular processes. Thus, U.S. Pat. No. 3,234,140 describes treatment baths of diluted hydrogen peroxide base for the bleaching of cellulosic materials. The pH of these baths is adjusted to a value ranging between 7.5 and 12.5 and they are stabilized with organic phosphonic acids. The hydrogen peroxide used for such application is of industrial quality, i.e., not free from carbon compounds and metals arising from its process of preparation.

SUMMARY AND OBJECTS OF THE INVENTION

In view of the foregoing limitations and shortcomings of hydrogen peroxide disinfection or sterilization systems of the related art, as well as other disadvantages not specifically mentioned above, it should be apparent that there still exists a need in the art for a disinfection/sterilization system based on hydrogen peroxide which will not cause fouling of spraying systems or the jamming of moving parts of such systems. It is, therefore, a primary object of the present invention to provide a process for the treatment of an article by spraying an aqueous solution of hydrogen peroxide which permits an appreciable reduction in the jamming of movable mechanical parts and the fouling of the spraying system, and therefore avoids in this manner the overly frequent cleaning of such system before it clogs-up.

Another object of the invention is a novel aqueous hydrogen peroxide solution which is stabilized.

In a first aspect, the present invention relates to a process for disinfecting or sterilizing an article comprising spraying on at least one surface of the article an aqueous hydrogen peroxide solution including an organic phosphonic acid in an amount effective to stabilize the hydrogen peroxide solution, the solution being free of other stabilizing agents, i.e., the solution is stabilized exclusively by organic phosphonic acids.

In a second aspect, the present invention relates to an aqueous hydrogen peroxide solution of high purity comprising (i) an organic phosphonic acid in an amount effective to stabilize the hydrogen peroxide solution, the solution being free of other stabilizing agents, and (ii) a dry residue of less than 120 mg/kg, the solution having a conductivity less than 120 µS/cm.

With the foregoing and other objects, advantages, and features of the invention that will become hereinafter apparent, the nature of the invention may be more clearly understood by reference to the following detailed description of the invention and to the appended claims,

DETAILED DESCRIPTION OF PREFERRED EMBODIMENTS

This process permits in a very surprising manner the reduction in the fouling of the spraying system and thus avoids the need for cleaning such system every day or, at best, every two days. It has thus been observed that a weekly cleaning of the spraying system could be quite sufficient, while avoiding all risk of clogging. In addition, the organic phosphonic acids utilized as the only stabilizing agents confer very good stability to the aqueous hydrogen peroxide solution.

In the context of the present invention, the organic phosphonic acid is:

(i) a compound of the formula (I):

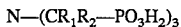

in which $R_1$ and $R_2$, which may be identical or different, are hydrogen or a $C_1$–$C_4$ alkyl radical; or (ii) a compound of the formula (II):

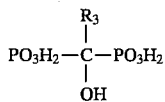

in which $R_3$ is hydrogen or a $C_1$–$C_4$ alkyl radical.

By way of compounds of formula (II) above, there can be mentioned 1-hydroxyethylene-1,1-diphosphonic acid.

The preferred organic phosphonic acid for the implementation of the process according to the invention is amino-tris-methylene-phosphonic acid, of the formula:

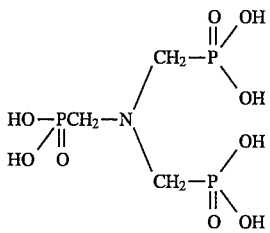

An organic phosphonic acid more particularly preferred is 1-hydroxyethylene-1,1, diphosphonic acid.

Typically, the concentration of the organic phosphonic acid in the aqueous hydrogen peroxide solution is, according to the invention, less than 50 mg/kg and preferably, it ranges between 10 and 30 mg/kg.

The concentration of hydrogen peroxide in the aqueous solution is an amount effective to disinfect or sterilize the article to be treated and advantageously ranges between 15% and 70%, by weight, preferably between 30% and 40% by weight, and more preferably this concentration is about 35% by weight.

According to the invention, the apparent pH of the aqueous hydrogen peroxide solution utilized can be less than 3, preferably ranging between 1 and 2.7.

According to a particularly advantageous aspect of the process of the invention, the stabilized aqueous hydrogen peroxide solution is of high purity. Such aqueous solutions advantageously contain a dry residue, measured after evaporation at 110° C., of less than 100 mg/kg, and preferably ranging between 20 and 35 mg/kg. Besides, the conductivity of such a high purity solution is less than 120 µS/cm, and preferably, it ranges between 60 and 100 µS/cm; most preferably, this conductivity is about 80 µS/cm.

These aqueous hydrogen peroxide solutions stabilized with an organic phosphonic acid having high purity can be obtained starting from an aqueous hydrogen peroxide solution which is itself pure, i.e., has carbonaceous compounds and metallic impurities substantially removed therefrom. This can be prepared according to processes well known to persons skilled in the art, for example by distillation of an aqueous hydrogen peroxide solution of industrial quality.

When the treatment process according to the present invention includes the disinfection or sterilization of an article, the aqueous hydrogen peroxide solution is advantageously sprayed hot onto the article. Thus, the temperature of this aqueous hydrogen peroxide solution at the outlet of the spraying system can be made greater than 70° C., and preferably at a temperature ranging between 190° C. and 220° C. At temperatures of this order, the aqueous hydrogen peroxide solution is present under the form of a mist, which comes into contact with the surface of the article to be treated.

The article treated according to the process of the invention can be a foodstuff or an article of aluminum, cardboard or of a polymer such as polyethylene terephthalate or, preferably, polyethylene. This article can more particularly comprise a packaging for a foodstuff, a cosmetic product or a pharmaceutical product. The process according to the invention is more particularly suited to the disinfection or the sterilization of such articles.

According to another aspect, the invention relates to an aqueous hydrogen peroxide solution of high purity, having a dry residue which is less than 120 mg/kg, preferably ranging between 20 and 50 mg/kg, this solution being stabilized exclusively by an organic phosphonic acid. It is particularly advantageous that this aqueous solution have a conductivity less than 120 µS/cm, preferably ranging between 60 and 100 µS/cm, and more preferably on the order of 80 µS/cm.

Such an aqueous solution, substantially free of all stabilizing agents other than the organic phosphonic acids, is perfectly suited for carrying out the process of the invention described above.

By way of organic phosphonic acids which can be used to stabilize the aqueous hydrogen peroxide solution according to the invention, there can be cited compounds of formula (I) and (II) mentioned above.

The concentration of the phosphonic acid in the aqueous solution is generally less than 50 mg/kg and preferably it ranges between 10 and 30 mg/kg. The concentration by weight of hydrogen peroxide can range between 15 and 70% and preferably between 30 and 40%, and yet more preferably, it is on the order of 35%. The pH of the aqueous solution is advantageously less than 3 and preferably ranges between 1 and 2.5.

The aqueous hydrogen peroxide solution according to the invention can be prepared starting from an aqueous hydrogen peroxide solution of high purity to which there is added a chosen quantity of an organic phosphonic acid such as those indicated above. When the aqueous hydrogen peroxide solution of high purity has a significant concentration of hydrogen peroxide, for example a concentration of 35 or of 70%, it can if necessary be diluted with water which itself is of high purity, for example distilled water.

The examples which follow have as their object the illustration of the present invention.

EXAMPLE 1

In order to sterilize packaging materials having a surface comprised of a sheet of polyethylene, there is employed a spraying system including a spraying jet followed by a Thermocoax having an internal diameter of 3.5 cm and a length 25 cm. Each package is sprayed with 0.75 ml of an aqueous hydrogen peroxide solution distilled to 35% by weight and stabilized by amino-tris-methylenephosphonic acid (ATMP) at a concentration of 26 mg/kg. At the outlet of the Thermocoax, the aqueous solution is at 200° C.

The dry residue of this stabilized aqueous solution, measured after evaporation at 110° C., is 20 mg/kg, its conductivity is 80 µS/cm and its apparent pH is 2.5.

After more than a week of use, no blockage of the spraying system was observed. The employment of the aqueous hydrogen peroxide solution described above permitted the spraying system to be cleaned only once per week.

EXAMPLE 2 (Comparative)

Example 1 was reproduced with an aqueous hydrogen peroxide solution similarly distilled to 35%, but stabilized with 9 mg/kg of a 40% aqueous sodium stannate solution. The dry residue of this aqueous solution, measured after evaporation at 110° C, is 23 mg/kg, its conductivity is 40 µS/cm and its pH is 3.1.

The use of this aqueous solution leads to a blocking of the spraying system at the end of about 35 hours. Under these conditions it is necessary to clean the spraying system once every 24 hours.

EXAMPLE 3 (Comparative)

Example 1 was reproduced with an aqueous hydrogen peroxide solution similarly distilled but stabilized with 18 mg/kg of sodium pyrophosphate acid and 2.2 mg/kg of a 40% aqueous solution of sodium stannate. The pH of the solution is 3.1.

The use of this solution leads to a blocking of the spraying system at the end of about 45 hours, which requires that the system be cleaned once every 24 hours.

EXAMPLE 4

Example 1 was reproduced with a solution of hydrogen peroxide solution similarly distilled to 35% but stabilized with 1-hydroxyethylene-1,1,diphosphonic acid (AHEP) at a concentration of 26 mg/kg.

The dry residue of this stabilized solution, measured after evaporation at 110° C., is 25 mg/kg and its pH is 2.6.

After more than a week of use, no blockage of the spraying system was observed. When the spraying system was cleaned by means of classical cleaning agents, it was observed that the cleaning was easier with the hydrogen peroxide solution stabilized with 26 mg/kg of AHEP than with 26 mg/kg of ATMP (solution of Example 1).

It is understood here that by "easier cleaning", is meant better dissolution of the deposit in the cleaning agents, a deposit which is more friable and a more homogenous distribution of the deposit on the different pieces of the spraying system.

EXAMPLE 5

In order to determine the stability of different aqueous hydrogen peroxide solutions, there was measured the relative loss in $H_2O_2$ content after 16 hours at 96° C.

The aqueous hydrogen peroxide solution distilled to 35% before addition of the stabilizing agent, used in Examples 1 to 4, had under these conditions a relative loss of 5.4%.

The stabilized aqueous solutions utilized in examples 1, 2, 3 and 4 had relative losses of, respectively, 1.1%, 1%, 3% and 1.1%.

Although only preferred embodiments of the invention are specifically illustrated and described above, it will be appreciated that many modifications and variations of the present invention are possible in light of the above teachings and within the purview of the appended claims without departing from the spirit and intended scope of the invention.

What is claimed is:

1. A process for disinfecting or sterilizing an article, using a spraying system, comprising spraying on at least one surface of said article a stabilized aqueous hydrogen peroxide solution which comprises a disinfecting or sterilizing amount of hydrogen peroxide and an organic phosphonic acid in an amount effective to stabilize said hydrogen peroxide solution, said hydrogen peroxide solution being free of other stabilizing agents; wherein after more then a week of use, no blockage of the spraying system is observed.

2. The process according to claim 1 wherein the organic phosphonic acid is:

(i) a compound of formula (I):

in which $R_1$ and $R_2$, which may be identical or different, are hydrogen or a $C_1$–$C_4$ alkyl radical, or (ii) a compound of formula (II):

in which $R_3$ is hydrogen or a $C_1$–$C_4$ alkyl radical.

3. The process according to claim 2, wherein said organic phosphonic acid is amino-tris-methylene-phosphonic acid.

4. The process according to claim 2, wherein said organic phosphonic acid is 1-hydroxy ethylene 1,1-diphosphonic acid.

5. The process according to claim 1, wherein the concentration of organic phosphonic acid in said aqueous hydrogen peroxide solution is less than 50 mg/kg.

6. The process according to claim 5, wherein the concentration of organic phosphonic acid in said aqueous hydrogen peroxide solution ranges between 10 and 30 mg/kg.

7. The process according to claim 1, wherein the concentration by weight of hydrogen peroxide in said aqueous hydrogen peroxide solution ranges between 15% and 70%.

8. The process according to claim 7, wherein the concentration by weight of hydrogen peroxide in said aqueous hydrogen peroxide solution ranges between 30% and 40%.

9. The process according to claim 8 wherein the concentration by weight of hydrogen peroxide in said aqueous hydrogen peroxide solution is about 35%.

10. The process according to claim 1, wherein said aqueous hydrogen peroxide solution has a dry residue content of less than 120 mg/kg.

11. The process according to claim 10, wherein said aqueous hydrogen peroxide solution has a dry residue content between 20 and 50 mg/kg.

12. The process according to claim 1, wherein said aqueous hydrogen peroxide solution has a conductivity of less than 120 µS/cm.

13. The process according to claim 12, wherein said conductivity is between 60 and 100 µS/cm.

14. The process according to claim 13, wherein said conductivity is about 80 µS/cm.

15. The process according to claim 1, further comprising heating said aqueous hydrogen peroxide solution to a temperature greater than 70° C.

16. The process according to claim 15 wherein said aqueous hydrogen peroxide solution is heated to a temperature between 190° C. and 220° C.

17. The process according to claim 1, wherein said aqueous hydrogen peroxide solution has a pH of less than 3.

18. The process according to claim 17, wherein said aqueous hydrogen peroxide solution has a pH between 1 and 2.5.

19. The process according to claim 1, wherein the article is a foodstuff or a packaging material.

20. The process according to claim 19, wherein said packaging material is cardboard, aluminum or a polymeric material.

21. The process according to claim 20, wherein said polymeric material is polyethylene or polyethylene-terephthalate.

* * * * *